US012791690B2

(12) United States Patent
Keim et al.

(10) Patent No.: US 12,791,690 B2
(45) Date of Patent: Nov. 10, 2026

(54) ELECTROMECHANICAL CONNECTOR COVER FOR AN ELECTROMECHANICAL CONNECTOR OF AN ULTRASOUND IMAGING PROBE

(71) Applicant: GE Precision Healthcare LLC, Waukesha, WI (US)

(72) Inventors: Melanie Ann Keim, Pennsylvania Furnace, PA (US); Ethan Lee White, State College, PA (US); Nathan Patrick McCarraher, Oxford, PA (US); Sarah Ann Bubbenmoyer, Lenhartsville, PA (US); Gabriela Marie Fortuno, Huntingtown, MD (US); Benjamin Philippe Roy, Coatesville, PA (US); Brandon Paul McKnerney, Southington, CT (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 151 days.

(21) Appl. No.: 18/641,021

(22) Filed: Apr. 19, 2024

(65) Prior Publication Data

US 2025/0327915 A1 Oct. 23, 2025

(51) Int. Cl.
*G01S 7/52* (2006.01)
*A61B 8/00* (2006.01)

(52) U.S. Cl.
CPC ......... *G01S 7/52082* (2013.01); *A61B 8/4411* (2013.01)

(58) Field of Classification Search
None
See application file for complete search history.

(56) References Cited

U.S. PATENT DOCUMENTS

| | | | | | |
|---|---|---|---|---|---|
| 2,972,001 | A | * | 2/1961 | Clingenpeel ........ | H01M 50/308 429/185 |
| 5,494,038 | A | * | 2/1996 | Wang .................. | A61B 8/4281 73/644 |
| 5,678,551 | A | * | 10/1997 | Stevens ................ | A61B 8/4455 600/475 |
| 5,997,481 | A | * | 12/1999 | Adams ................. | A61B 8/4281 600/459 |
| 6,182,341 | B1 | | 2/2001 | Talbot et al. | |

(Continued)

FOREIGN PATENT DOCUMENTS

| | | | |
|---|---|---|---|
| CN | 116098647 | A | 5/2023 |
| EP | 2560469 | A1 | 2/2013 |

(Continued)

*Primary Examiner* — Jonathan D Armstrong
(74) *Attorney, Agent, or Firm* — Daugherty & Del Zoppo, Co. LPA

(57) ABSTRACT

An electromechanical connector cover for covering an electromechanical connector of an ultrasound imaging probe includes a three-dimensional container with a cavity configured to receive the electromechanical connector. The cavity includes a rim configured to provide a hermetic seal with the received electromechanical connector. The electromechanical connector cover further includes at least one side with at least one opening. The electromechanical connector cover further includes a membrane disposed in the cavity and adjacent to the at least one opening. The membrane is liquid-proof and air-permeable.

10 Claims, 9 Drawing Sheets

(56) References Cited

U.S. PATENT DOCUMENTS

| | | | | |
|---|---|---|---|---|
| 8,012,095 | B2 | 9/2011 | Prager et al. | |
| 8,939,333 | B2 * | 1/2015 | Ivarez | A45F 5/00 224/272 |
| 8,945,013 | B2 | 2/2015 | Oakley et al. | |
| 9,214,152 | B2 | 12/2015 | Kunkel et al. | |
| 9,842,583 | B2 | 12/2017 | Kunkel et al. | |
| 2003/0009100 | A1 * | 1/2003 | Derendorf | A61B 5/14528 600/424 |
| 2007/0276241 | A1 * | 11/2007 | Park | A61B 8/4422 600/437 |
| 2007/0276253 | A1 * | 11/2007 | Park | A61B 17/3403 600/461 |
| 2013/0087593 | A1 * | 4/2013 | Ivarez | A45F 5/00 224/576 |
| 2014/0243677 | A1 * | 8/2014 | Johnson | A61B 46/10 600/459 |
| 2020/0069286 | A1 * | 3/2020 | Weasler | A61B 8/4422 |
| 2020/0383660 | A1 * | 12/2020 | Rothberg | A61B 8/4281 |

FOREIGN PATENT DOCUMENTS

| | | | |
|---|---|---|---|
| JP | 2008212501 A | * | 9/2008 |
| JP | 2019526756 A | | 9/2021 |

* cited by examiner

ELECTROMECHANICAL CONNECTOR COVER FOR AN ELECTROMECHANICAL CONNECTOR OF AN ULTRASOUND IMAGING PROBE

FIELD

The following generally relates to ultrasound imaging, and finds particular application to an electromechanical connector cover for an electromechanical connector of an ultrasound imaging probe, and is also amenable to other electromechanical connectors.

BACKGROUND

Ultrasound imaging provides real-time imaging of information about the interior of an object or a subject such as tissue, organs, etc. An example ultrasound imaging system includes an ultrasound imaging probe and a console. The ultrasound imaging probe houses a transducer array and includes at least a handle, a cable, and an electromechanical connector at the end of the cable. The console includes signal processing hardware and software, a user interface, a display monitor, and a complementary electromechanical connector. The ultrasound imaging probe and the console interface via the electromechanical connector and complementary electromechanical connector.

The transducer array is configured to transmit a pressure wave and receive echoes produced in response to the pressure wave interacting with structure such as tissue, blood cells, etc. The echoes are converted to analog signals and conveyed to the console through the electromechanical connector and complementary electromechanical connector interface. In one instance, the analog signals are amplified, digitized, and beamformed to produce scan lines of radio frequency (RF) data. The scan lines are processed (e.g., band-pass filtering, envelope detection, logarithmic compression, etc.), scan converted, and displayed as a 2-D (B-mode) ultrasound image. The echo signals can also be processed for A-mode, C-plane, Doppler, color-flow, elastography, and/or other applications.

Some ultrasound imaging probes are employed in connection with invasive procedures such as laparoscopic procedures. A laparoscopic procedure is a procedure performed within a cavity of a patient, such as the abdomen or pelvis, through small incisions. A laparoscopic ultrasound imaging probe further includes an elongated shaft between the probe head and the handle. Some laparoscopic ultrasound imaging probes further include an articulating member at the shaft and probe head interface, with a rubber boot seal or the like over the articulating member. The articulating member allows a user to move the transducer array within the cavity, independent of the probe, and the rubber boot seal protects the articulating member from the environment.

Ultrasound imaging probes utilized during invasive procedures, such as laparoscopic procedures, come into contact with bodily fluids. As such, after an invasive procedure, the ultrasound imaging probe is reprocessed, including cleaning, disinfection and sterilization. An example reprocessing process includes submerging, during cleaning and disinfection, the ultrasound imaging probe, including the electromechanical connector, in an environment that includes chemicals, such as hydrogen peroxide, etc., and exposing, during sterilization, the ultrasound imaging probe, including the electromechanical connector, in an environment that includes a pressure difference such as a vacuum.

Generally, ultrasound imaging probes are hermetically sealed except for part of the electromechanical connector, which, as briefly discussed above, is configured to electrically and mechanically engage a complementary electromechanical connector of the console. As such, for cleaning and disinfection, an electromechanical connector cover is installed over the electromechanical connector of the ultrasound imaging probe. The electromechanical connector cover is configured to inhibit an ingress of liquids such as the chemicals utilized for the cleaning and disinfection portion of the reprocessing (i.e., the electromechanical connector cover is liquid-proof). Once the electromechanical connector cover is installed over the electromechanical connector, the ultrasound imaging probe can be safely submerged in the chemicals for cleaning and disinfection.

The electromechanical connector cover not only inhibits an ingress of liquids through electromechanical connector of an otherwise hermetically sealed ultrasound imaging probe, but further inhibits an egress of air out the ultrasound imaging probe (i.e., the electromechanical connector cover is air-proof). However, the sterilization process creates an environment that includes a pressure difference such as a vacuum. As such, before sterilization, the electromechanical connector cover is removed from the electromechanical connector. Otherwise, the pressure difference between the inside of the ultrasound imaging probe and the surrounding environment may result in damage to the ultrasound imaging probe such as bursting of the rubber boot seal of the articulating member, etc.

Should an ultrasound imaging probe with the electromechanical connector cover installed thereon inadvertently be subjected to the sterilization and the rubber boot seal burst, the compromised ultrasound imaging probe could not be utilized for an invasive procedure of a patient until the ultrasound imaging probe were repaired or replaced. An exiting approach to prevent such an event from occurring includes specifying in a maintenance manual reprocessing instructions that indicate that the electromechanical connector cover should be installed on the electromechanical connector during cleaning and disinfection but not for sterilization, where the electromechanical connector cover should be removed after cleaning and disinfection and before sterilization. Additionally, similar instructions have been placed on the electromechanical connector cover itself.

Unfortunately, the above-noted approach of including reprocessing instructions in the maintenance manual (and optionally the electromechanical connector cover) indicating when to install and remove the electromechanical connector cover relies on a customer removing the electromechanical connector cover between disinfection and sterilization, and a customer may unintentionally or inadvertently not remove the electromechanical connector cover before sterilization, leading to bursting of the rubber boot seal, downtime of the ultrasound imaging probe, and additional costs associated with repairing or replacing the ultrasound imaging probe. In view of at least the foregoing, there is an unresolved need for an improved approach in connection with reprocessing an ultrasound imaging probe.

SUMMARY

Aspects of the application address the above matters, and others. This summary introduces concepts that are described in more detail in the detailed description. It should not be used to identify essential features of the claimed subject matter, nor to limit the scope of the claimed subject matter.

In one aspect, an electromechanical connector cover for covering an electromechanical connector of an ultrasound imaging probe includes a three-dimensional container. The three-dimensional container includes a cavity configured to receive the electromechanical connector. The cavity includes a rim configured to provide a hermetic seal with the received electromechanical connector. The electromechanical connector cover further includes at least one side with at least one opening. The electromechanical connector cover further includes a membrane disposed in the cavity and adjacent to the at least one opening. The membrane is liquid-proof and air-permeable.

In another aspect, a system includes ultrasound imaging system. The ultrasound imaging system includes an ultrasound imaging probe, a console and an electromechanical connector cover. The ultrasound imaging probe includes an elongated shaft, a probe head housing a set of transducing elements, wherein the probe head disposed at a first end of the elongated shaft, a handle disposed at a second opposing end of the elongated shaft, and an electromechanical connector attached to the handle via a cable. The console includes a complementary electromechanical connector configured to mechanically and electrically engage the electromechanical connector to provide electrical communication between the console and the ultrasound imaging probe, and components configured to process signals routed from the set of transducing elements via the electromechanical connector and the complementary electromechanical connector. The electromechanical connector cover is removably installable over the electromechanical connector. An interface between the installed electromechanical connector and the electromechanical connector cover provides a hermetic seal. The electromechanical connector cover is liquid-proof and air-permeable.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings in which like references indicate similar elements.

Figure 25:
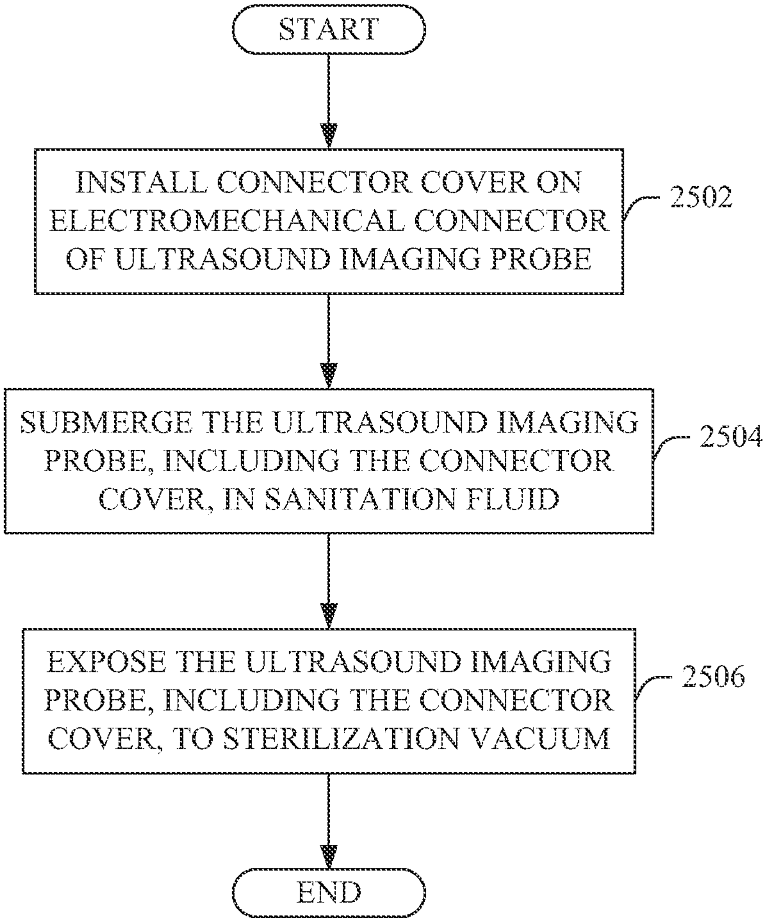

FIG. 25 illustrates another non-limiting example of a flow chart for a computer-implemented method based at least on image characteristics, in accordance with an embodiment(s) herein.

DETAILED DESCRIPTION

Embodiments of the present disclosure will now be described, by way of example, with reference to the figures, in which an ultrasound imaging system and/or method includes utilizing an electromechanical connector cover that is air-permeable and liquid-proof to cover a portion of an electromechanical connector of an ultrasound imaging probe during reprocessing that involves both cleaning and disinfection with liquids and sterilization employing a pressure difference. As discussed above, ultrasound imaging provides real-time imaging of information about the interior of an object or a subject such as tissue, organs, etc., and a laparoscopic ultrasound imaging probe is configured for invasive procedures (e.g., an ablation, biopsy, etc.) performed in a cavity of a patient, such as the abdomen or pelvis, using small incisions (i.e., laparoscopic procedures). An example of such an ultrasound imaging probe is a laparoscopic ultrasound imaging probe including an articulation member, with a rubber boot seal, that allows a user to move the transducer array within the cavity, independent of the ultrasound imaging probe.

As discussed herein, with invasive procedures such as laparoscopic procedures the laparoscopic ultrasound imaging probe contacts bodily fluids. As such, after an invasive procedure, the ultrasound imaging probe is reprocessed through cleaning, disinfection and sterilization, which includes submerging the ultrasound imaging probe, including the electromechanical connector, in an environment that includes chemicals such as hydrogen peroxide, etc. and in an environment that includes pressure differences such as a vacuum. Also discussed herein, an electromechanical connector cover is installed over part of the electromechanical connector ultrasound imaging probe to inhibit an ingress of liquids such as the chemicals utilized for the cleaning and disinfection portion of the reprocessing, and then removed for sterilization to allow egress of gasses such as air out of the electromechanical connector under the vacuum of the sterilization portion of the reprocessing.

As discussed herein, if the electromechanical connector cover is not removed before sterilization, a pressure difference generated during sterilization between the inside of the ultrasound imaging probe and the surrounding environment may result in damaging the ultrasound imaging probe such as bursting of the rubber boot seal of the articulating member. An existing approach to prevent such an event from occurring includes specifying in the maintenance manual (and optionally on the electromechanical connector cover itself) instructions that indicate that the electromechanical connector cover should be installed on the electromechanical connector during cleaning and disinfection and that the electromechanical connector cover should not be installed on the electromechanical connector during sterilization, which is subject to human error, which may result in ultrasound imaging probe downtime and/or increased cost associated with repairing and/or replacing the compromised ultrasound imaging probe.

Described herein is an approach in which the connector cover includes a member housing a liquid-proof and an air-permeable membrane, which inhibits ingress of fluid during the cleaning and disinfection process and allows egress of gas during the sterilization process. As such, the electromechanical connector cover can remain on during the entire reprocessing process, mitigating damage to the ultrasound imaging probe, such as damaging the rubber boot seal of the articulating member during sterilization when the electromechanical connector cover is on, which can reduce downtime of a compromised ultrasound imaging probe and/or can reduce overall correction maintenance cost associated with repairing and/or replacing a compromised ultrasound imaging probe.

Figure 1:
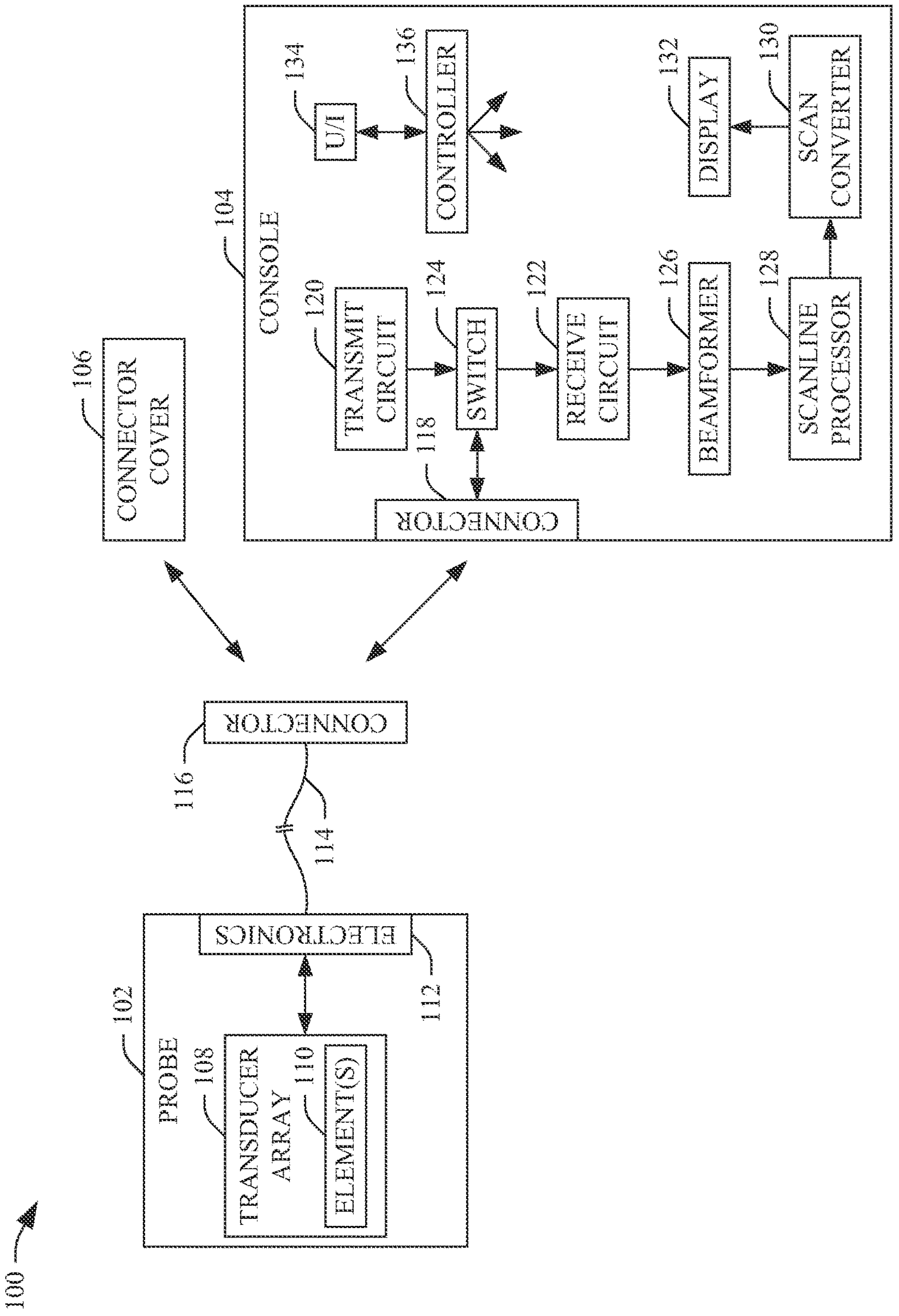
FIG. 1 schematically illustrates a non-limiting example of an ultrasound imaging system that includes an ultrasound imaging probe having an inline or cable electromechanical connector and a console having a complementary electromechanical connector, in accordance with an aspect of an embodiment(s) herein.

Initially referring to FIG. 1, a non-limiting example of an ultrasound system 100 is schematically illustrated. The ultrasound system 100 includes an ultrasound imaging probe 102, a console 104, and an electromechanical connector cover 106.

The ultrasound imaging probe 102 includes transducer array 108. The transducer array 108 includes one or more transducer elements 110. Examples of suitable arrays include 64, 128, 192, 256, and/or other arrays, including larger and smaller arrays, one dimensional (1-D) or two dimensional (2-D), etc. The transducer array 108 can be linear, curved, and/or otherwise shaped, fully populated, sparse and/or a combination thereof, etc. The one or more transducer elements 110 are configured to convert an excitation electrical signal to an ultrasound pressure field and convert a reflected ultrasound pressure field to an electrical signal.

By way of non-limiting example, the one or more transducer elements 110 can be selectively excited via an excitation electrical (pulsed) signal, which causes at least a sub-set of the one or more transducer elements 110 to transmit an ultrasound pressure field into an examination or scan field of view. The ultrasound pressure field may include a focused ultrasound beam, a defocused (spherical) wave, and/or other ultrasound signal. The one or more transducer elements 110 receive echo signals and generate analog electrical signals indicative thereof. The echo signals are generated in response to the transmitted ultrasound pressure field interacting with structure, such as tissue and/or blood cells flowing in a portion of a vessel.

The ultrasound imaging probe 102 further includes electronics 112, a cable 114 and an inline or cable electromechanical connector 116. The electronics 112 are housed in a housing of the ultrasound imaging probe 102. A first end of the cable 114 is in electrical communication with the electronics 112. A second end of the cable 114 is in electrical communication with the inline or cable electromechanical connector 116. In one instance, the inline or cable electromechanical connector 116 is part of a plug and socket connector pair, e.g., a "male" plug including an outer housing and electrically conductive pins, individual or on a printed circuit board (PCB).

Figure 2:
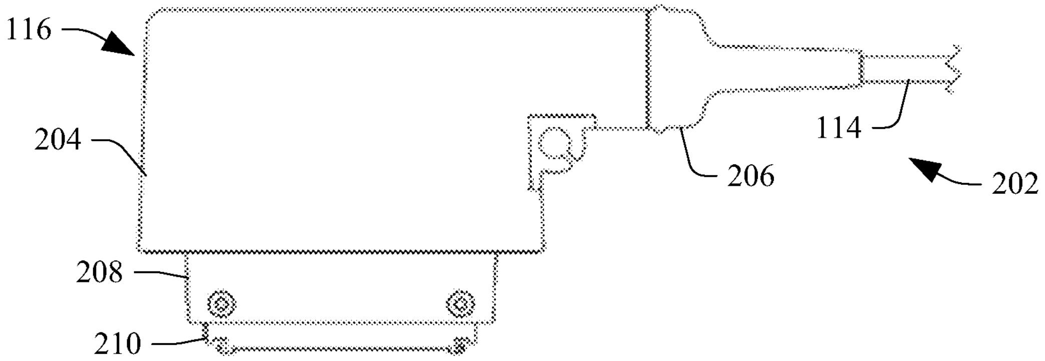
FIG. 2 schematically illustrates a non-limiting example of the inline or cable electromechanical connector of the ultrasound imaging system, in accordance with an aspect of an embodiment(s) herein.

Briefly turning to FIG. 2, an example of the inline or cable electromechanical connector 116 and part of the cable 114, including a second end 202 of the cable 114 in electrical communication with the inline or cable electromechanical connector 116, is schematically illustrated. Other electromechanical connector configurations are contemplated herein. The inline or cable electromechanical connector 116 includes a housing 204. The second end 202 of the cable 114 is attached to the housing 204 via a strain relief connection 206, which relieves stress at the connection to reduce or prevent unintentional disconnection of the inline or cable electromechanical connector 116 from the housing 204. The cable 114 routes electrically conductive wires from the console 104 to the housing 204. The housing 204 houses electronics (not visible).

In one instance, the housing 204 houses a circuit board (not visible) that carries the electronics. The wires routed by the cable 114 are in electrical communication with the electronics in the housing 204 and route electrical signals between the transducer array 108 and the electronics. The inline or cable electromechanical connector 116 further includes a "male" plug 208 with a circuit board 210 carrying electrically conductive pins, etc. The electrically conductive pins, etc. are in electrical communication with the electronics in the housing 204. An example of such a connector is described in U.S. Pat. No. 11,510,646 B1, filed on Apr. 5, 2017, and entitled "Ultrasound imaging system probe cable and connector," the entirety of which is incorporated herein by reference.

Figure 3:
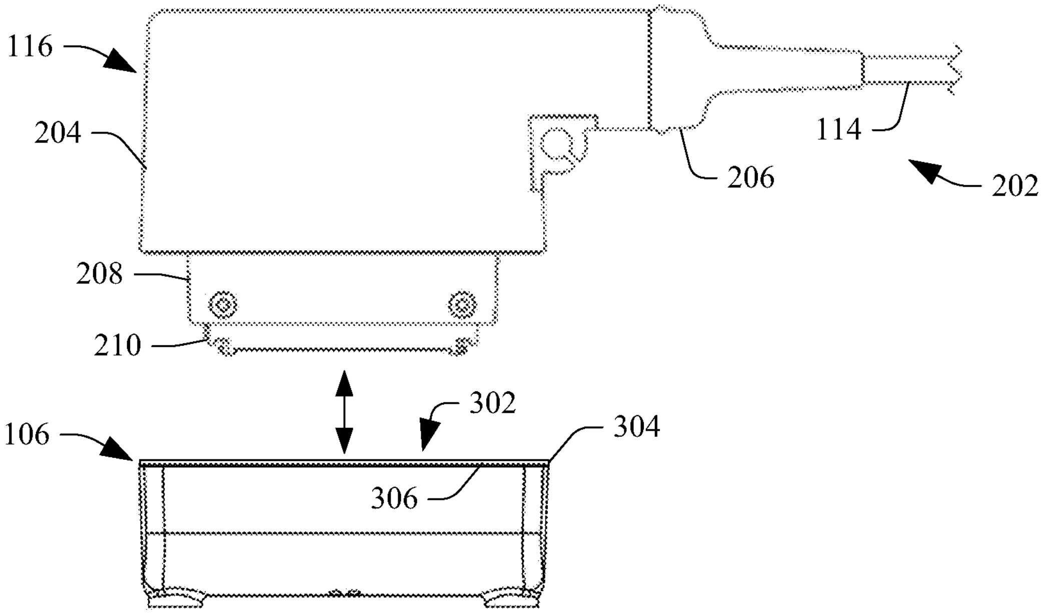
FIG. 3 schematically illustrates a non-limiting example of an electromechanical connector cover configured to cover exposed electromechanical components of the inline or cable electromechanical connector for reprocessing of the ultrasound imaging probe detached from the inline or cable electromechanical connector, in accordance with an aspect of an embodiment(s) herein.
Figure 4:
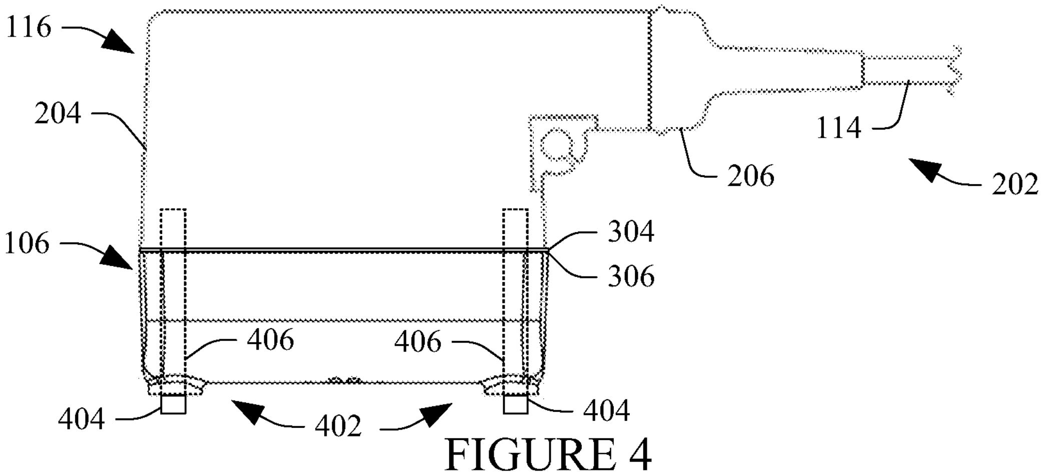
FIG. 4 schematically illustrates a non-limiting example of the electromechanical connector cover installed over the inline or cable electromechanical connector of the ultrasound imaging probe, in accordance with an aspect of an embodiment(s) herein.

Returning to FIG. 1, as briefly described above, an electromechanical connector cover 106 is utilized to cover exposed electromechanical elements, e.g., the plug 208 and the circuit board 210 (FIG. 2), of the inline or cable electromechanical connector 116 for cleaning and disinfection during reprocessing to inhibit an ingress of chemicals such as hydrogen peroxide, etc. that can compromise the ultrasound imaging probe 102. FIGS. 3 and 4 schematically illustrates an example of part of the ultrasound imaging probe 102 in connection with the electromechanical connector cover 106. FIG. 3 schematically illustrates a side view with the electromechanical connector cover 106 detached from the ultrasound imaging probe 102, and FIG. 4 schematically illustrates a side view with the electromechanical connector cover 106 installed on the inline or cable electromechanical connector 116 of the ultrasound imaging probe 102.

In general, the electromechanical connector cover 106 includes a cavity 302 (FIG. 3) configured to enclose the plug 208 (FIG. 2), including the circuit board 210 (FIG. 2) carrying the electrically conductive pins. In some instances, the electromechanical connector cover 106 is configured to receive a mechanical seal 304, such as a gasket, an O-ring, etc., at a rim 306 of the cavity. The electromechanical connector cover 106 is attached to the inline or cable electromechanical connector 116, with the mechanical seal 304 therebetween to create a hermetic seal at the rim 306 (FIG. 4) between the electromechanical connector cover 106 and the inline or cable electromechanical connector 116. The electromechanical connector cover 106 can be variously attached to the inline or cable electromechanical connector 116, e.g., via at least one mechanical fastener 402 such as a locking pin, a screw, a bolt, etc. In this example, the electromechanical connector cover 106 includes incudes multiple mechanical fasteners 402, each including a head 404 and a trunk 406.

As described in greater detail below, the electromechanical connector cover 106 is configured to concurrently inhibit an ingress of a fluid, such as the chemicals utilized during cleaning and disinfection, and allow an egress of gas such as air drawn out of the ultrasound imaging probe 102 by a vacuum environment during sterilization. In one instance, this allows the ultrasound imaging probe 102 to be processed throughout the entire reprocessing process without having to remove the electromechanical connector cover 106 for the sterilization portion of the reprocessing. In one instance, this mitigates damaging the ultrasound imaging probe 102 (e.g., bursting of the rubber boot seal of the articulating member) during sterilization.

Returning to FIG. 1, the console 104 includes a complementary electromechanical connector 118. The complementary electromechanical connector 118 is complementary to the inline or cable electromechanical connector 116 of the ultrasound imaging probe 102. For example, in one instance, the complementary electromechanical connector 118 is the other part of the plug and socket connector pair, e.g., a "female" socket including an outer housing and receptacle contacts. With this configuration, the complementary electromechanical connector 118 and the inline or cable electromechanical connector 116 are configured to electrically and mechanically engage and electrically communicate with each other.

The console 104 further includes a transmit circuit 120 configured to generate the excitation electrical signal provided to transducer array 108, via the complementary electromechanical connector 118 and the inline or cable electromechanical connector 116 interface, for transmitting the ultrasound pressure field. In one instance, this includes generating and conveying delays for individual elements 110 of the transducer array 108, e.g., for transmit focusing, beam steering, etc.

The console 104 further includes a receive circuit 122 configured to receive, via the inline or cable electromechanical connector 116 and the complementary electromechanical connector 118 interface, the analog electrical signals from the transducer elements 110. In one instance, the receive circuit 122 is further configured to pre-process the analog electrical signals, e.g., amplify, digitize, focus, and/or otherwise process the analog electrical signals. For example, in one instance the receive circuit 122 includes an amplifier and a corresponding analog to digital converter (ADC) for each element, where each amplifier amplifies a corresponding analog electrical signal from a micro-volt level to a voltage range of the ADC.

The console 104 further includes a switch 124 configured to switch between the transmit circuit 120 and the receive circuit 122, e.g., by electrically connecting the transmit circuit 120 to the transducer array 108 for a transmit operation and electrically connecting the receive circuit 122 to the transducer array 108 for a receive operation. In an alternative instance, separate switches are employed for each of the transmit circuit 120 and the receive circuit 122.

The console 104 further includes a beamformer 126. For receive operations, the beamformer 126 is configured to beamform, e.g., via delay-and-sum (e.g., a matched-filter beamformer, etc.) and/or other beamforming, the signals from the receive circuit 122 and construct a scanplane of scanlines of radiofrequency (RF) data (RF signal) for the echoes for each receive operation. With delay-and-sum beamforming, the digital signal for each element is delayed to align the signals in time, amplified, and then summed. The output of the beamformer 126 includes the RF signal.

The console 104 further includes a scanline processor 128 configured to perform other processing on the data such as filtering (e.g., via a Finite Impulse Response (FIR) filter, an Infinite Impulse Response (IIR) filter, etc.), time gain compensation (TGC), I/Q demodulation, envelope detection, logarithmic compression, noise rejection, and/or other processing, and output frames of data. When configured for I/Q demodulation, the scanline processor 128 down mixes the RF signal and, optionally, apply low pass filtering and/or decimation. This may include employing a Hilbert Transform, a combination of a Complex-Demodulation Band Pass Filter and optional decimation, and/or other processing.

The scanline processor 128 detects and extracts the envelope (e.g., an amplitude) of the I/Q signal (when the scanline processor 128 I/Q demodulates the RF signal) or the RF signal (when the scanline processor 128 does not I/Q demodulate the RF signal). In one instance, this is achieved using a Hilbert Transform and/or other approach. The scanline processor 128 compresses the extracted envelope, reducing the dynamic range thereof, e.g., to reduce the dynamic range to a predetermined display precision by a logarithmic (log)-based dynamic range compression and/or otherwise, and outputs a scanline. The scanline processor 128 outputs the processed scanlines as a frame/image (e.g., a B-mode image).

Additionally, or alternatively, the scanline processor 128 provides other processing, alone and/or in combination with other components. For instance, in another example, the scanline processor 128 is additionally, or alternatively, configured to process the echo signals received from the transducer array 108 of the ultrasound imaging probe 102 for A-mode applications, C-plane applications, Doppler applications, color-flow applications, elastography applications, and/or other applications.

The console 104 further includes a scan converter 130. The scan converter 130 is configured to scan convert the image into a coordinate system of an ultrasound system (US) display 132. The scan converter 130 can be configured to employ analog and/or digital scan converting techniques. The ultrasound system display 132 is integrated with the console 106. In another instance, ultrasound system display 132 is a separate and/or remote display monitor in electrical communication with the console 106.

The console 104 further includes a user interface (U/I) 134. The user interface 134 includes one or more input devices (such as a button, a knob, a slider, a touch screen, a mouse, a keyboard, etc.) and/or other input device, and/or one or more output devices such as a visible, audible, etc. indicator. The user interface 134 allows a user to control an operation of the ultrasound imaging system 100. The user interface 134 is shown integrated with the console 104. In another instance, the user interface 134 is a separate and/or remote keyboard, keypad, touch screen, etc. in electrical communication with the console 104.

The console 104 further includes a controller 136. The controller 136 includes a processor(s) such as a microprocessor (μP), a central processing unit (CPU), a graphics processing unit (GPU), etc., and memory, which stores the adaptive spatial compounding algorithm described herein. The controller 136 is configured to control one or more of the transmit circuit 120, the receive circuit 122, the switch 124, the beamformer 126, the scanline processor 128, the scan converter 130, the display 132, and the user interface 134. One or more of the components of the console 106 can be implemented in software and/or hardware.

Figure 5:
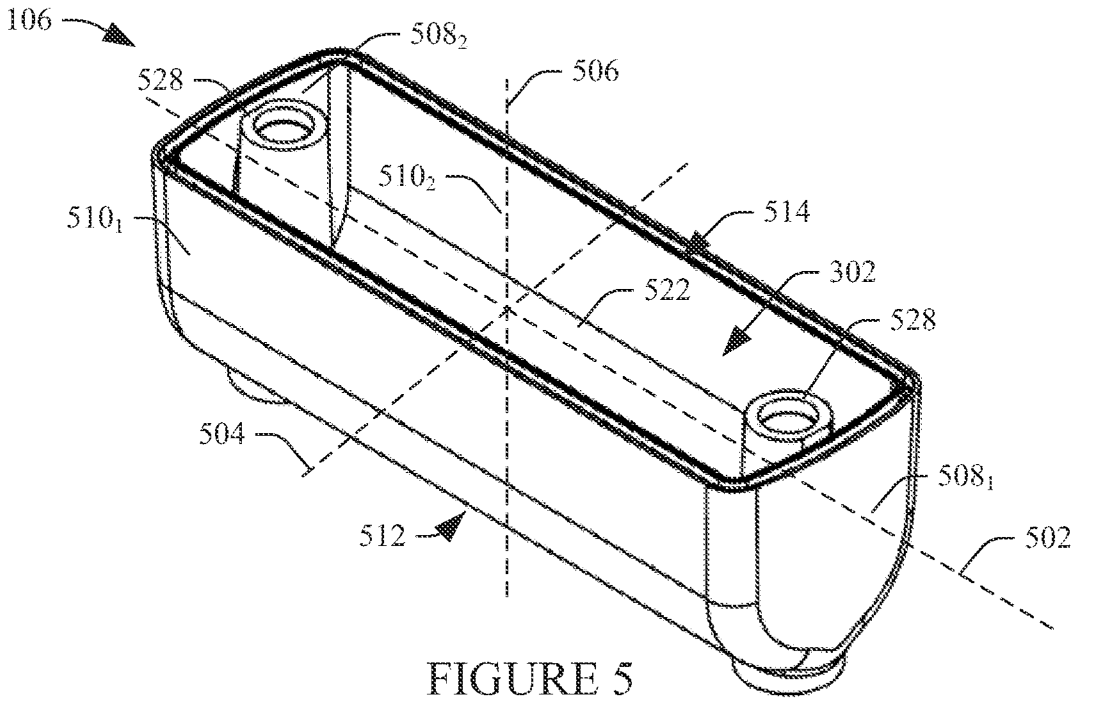
FIG. 5 schematically illustrates a perspective view of a non-limiting example of the electromechanical connector cover, in accordance with an aspect of an embodiment(s) herein.
Figure 6:
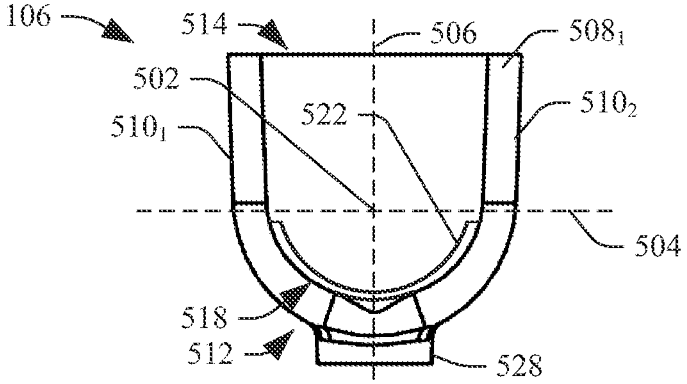
FIG. 6 schematically illustrates an end view of a non-limiting example of the electromechanical connector cover, in accordance with an aspect of an embodiment(s) herein.
Figure 7:
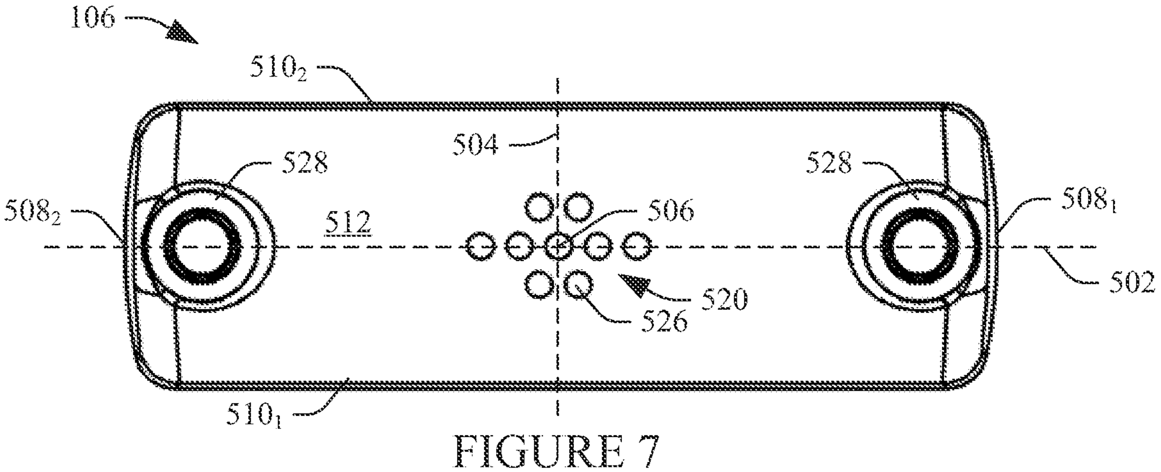
FIG. 7 schematically illustrates a front view of a non-limiting example of the electromechanical connector cover, in accordance with an aspect of an embodiment(s) herein.
Figure 8:
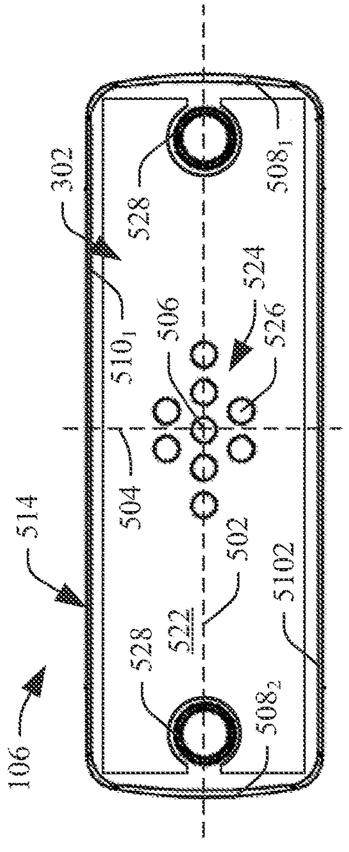
FIG. 8 schematically illustrates a rear view of a non-limiting example of the electromechanical connector cover looking into the cavity with a connector cover member installed in the cavity, in accordance with an aspect of an embodiment(s) herein.

Turning to FIGS. 5, 6, 7 and 8, an example of the electromechanical connector cover 106 is schematically illustrated. FIG. 5 schematically illustrates a perspective view of the electromechanical connector cover 106. FIG. 6 schematically illustrates an end view of the electromechanical connector cover 106. FIG. 7 schematically illustrates a front view of the electromechanical connector cover 106. FIG. 8 schematically illustrates a back or rear view of the electromechanical connector cover 106.

With reference to FIGS. 5, 6, 7 and 8, the electromechanical connector cover 106 is a three-dimensional (3-D) container with an opening to the cavity 302. The electromechanical connector cover 106 includes a first axis 502 along a length of the connector cover 106, a second axis 504 along a width of the connector cover 106, and a third axis 506 along a height of the electromechanical connector cover 106. The first axis 502, the second axis 504 and the third axis 506 are perpendicular to each other and define a coordinate system for the electromechanical connector cover 106.

The electromechanical connector cover 106 includes a first pair of opposing sides 508, including a first side $508_1$ and a second side $508_2$, which spatially opposes the first side $508_1$. The first side $508_1$ and the second side $508_2$ are at opposite ends of the first axis 502 (also referred to herein as the long axis 502) of the electromechanical connector cover 106. Each of the opposing sides $508_1$ and $508_2$ includes a planar surface with a generally "U" shaped profile. In other examples, the profile is otherwise shaped, e.g., square, rectangular, etc.

The electromechanical connector cover 106 includes a second pair of opposing sides 510, including a third side $510_1$ and a fourth side $510_2$, which spatially opposes the third side $510_1$. The third side $510_1$ and the fourth side $510_2$ are at opposite ends of the second axis 504 (also referred herein as the short axis 504) of the electromechanical connector cover 106. Each of the opposing sides $510_1$ and $510_2$ includes a planar surface with a generally "J" shaped profile, where the "J" is facing each other. In other examples, the profile is otherwise shaped, e.g., square, rectangular, etc.

Ends of tails of the "J" shaped profiles of the third side $510_1$ and the fourth side $510_2$ abut up against each other, and the stems of the "J" shaped profiles of the third side $510_1$ and the fourth side $510_2$ protrude parallel to each other and are spaced apart by a gap. Abutted together, the "J" shaped profiles form a "U" shaped profile. A bowl of the "U" shaped profile of the first side $508_1$ abuts one of the bowls created by abutting the third side $510_1$ and the fourth side $510_2$. A bowl of the "U" shaped profile of the second side $508_2$ abuts the other of the bowls created by abutting the third side $510_1$ and the fourth side $510_2$.

An outer region 512 of the bowls of the first side $508_1$, the side $508_2$, and the combination of the third side $510_1$ and the fourth side $510_2$ about a junction of the "J" shaped profiles provides a convex face. In another example, the out region 512 is planar or otherwise shape. Open ends of the bowls of the first side $508_1$, the side $508_2$, and the combination of the third side $510_1$ and the fourth side $510_2$ provide an opening at a rear side 514 of the connector cover 106 to the cavity 302 formed by the ascending walls of the bowls of the first side $508_1$, the side $508_2$, and the combination of the third side $510_1$ and the fourth side $510_2$ along the third axis 506 (also referred herein as the cavity axis 506) of the electromechanical connector cover 106.

An inner region 518 (FIG. 6) of the bowls of the first side $508_1$, the side $508_2$, and the combination of the third side $510_1$ and the fourth side $510_2$ about a junction of the "J" shaped profiles provides a concave surface. In another example, the inner region 518 is planar or otherwise shape. The electromechanical connector cover 106 includes a first set of openings 520 (FIG. 7) that extend from the inner concave surface 518 to the outer convex face 512, providing openings or material free regions from outside of the cover connector 106 to the cavity 302.

A member 522 (FIGS. 5 and 8) is disposed at the inner concave surface 518. As described in greater detail below, the member 522 includes a second set of openings 524 (FIG. 8) and a third set of openings (not visible in FIGS. 5-8) on an opposing side, and encloses a membrane 526, which is disposed between to the second set of openings 524 and a third set of openings and in fluid communication with the first set of openings 520 (FIG. 7) in the outer convex face 512, where the membrane 526 inhibits ingress of liquid and allows egress of gas. In one instance, the member 522 is affixed to the inner concave surface 518 via an adhesive such as an epoxy. In another instance, the member 522 is part of the mold of the electromechanical connector cover 106.

In this example, the electromechanical connector cover 106 further includes posts 528. The posts 528 are dimensioned to pass the trunks 406 (FIG. 4) of the mechanical fastener 402 (FIG. 4) to the inline or cable electromechanical connector 116 while inhibiting the heads 404 (FIG. 4) of the mechanical fastener 402 to pass. The trunks 406 of the mechanical fastener 402 are configured to engage complementary locking mechanisms of the inline or cable electromechanical connector 116, fastening the electromechanical connector cover 106 to the inline or cable electromechanical connector 116. In this example, the electromechanical connector cover 106 is configured to receive the mechanical seal 304 (FIG. 3) at the rim (FIG. 3) at the rear side 514, which hermetically seals the interface between the electromechanical connector cover 106 and the inline or cable electromechanical connector 116, providing a hermetic seal therebetween.

Figure 9:
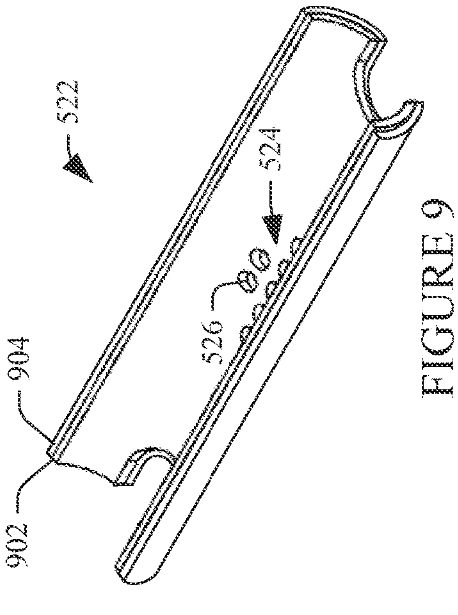
FIG. 9 schematically illustrates a perspective view of a non-limiting example of the connector cover member, in accordance with an aspect of an embodiment(s) herein.
Figure 10:
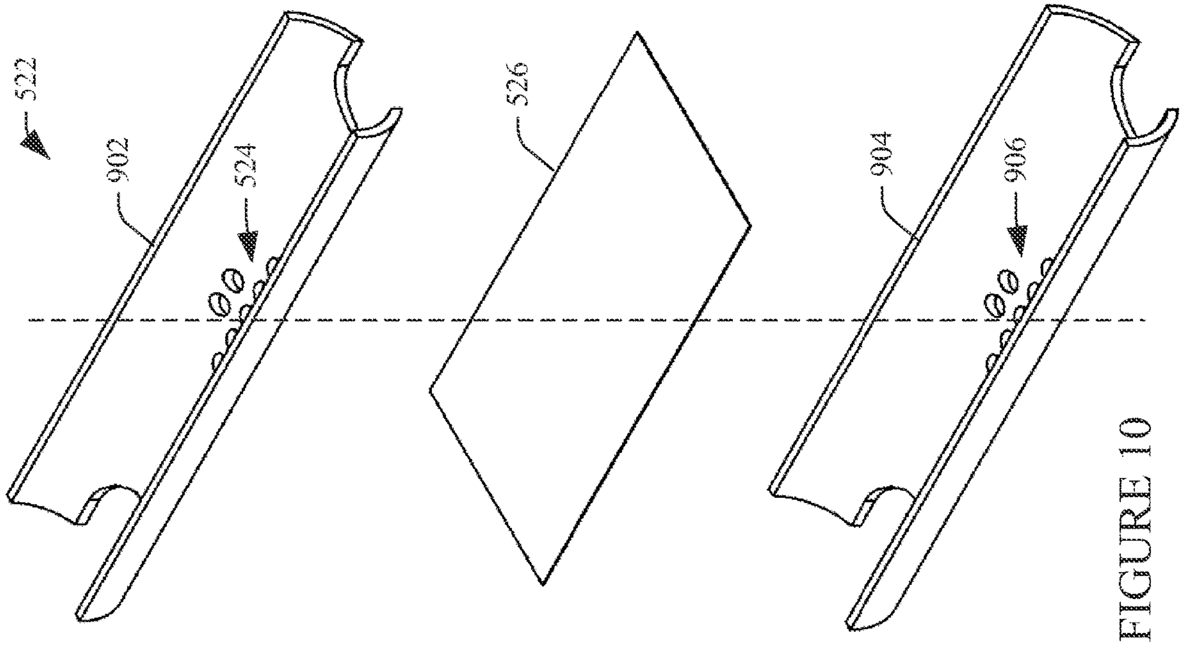
FIG. 10 schematically illustrates an exploded view of a non-limiting example of the connector cover member, in accordance with an aspect of an embodiment(s) herein.
Figure 11:
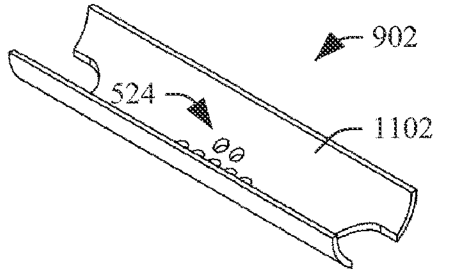
FIG. 11 schematically illustrates a top perspective view of a top portion of the connector cover member, in accordance with an aspect of an embodiment(s) herein.
Figure 12:
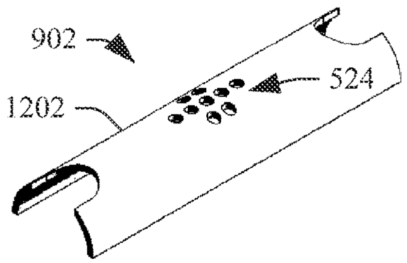
FIG. 12 schematically illustrates a bottom perspective view of the top portion of the connector cover member, in accordance with an aspect of an embodiment(s) herein.
Figure 13:
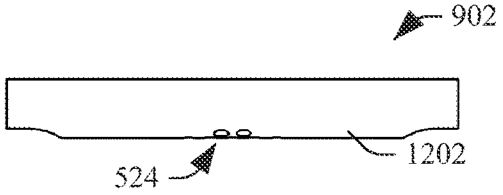
FIG. 13 schematically illustrates a side view from the top portion of the connector cover member, in accordance with an aspect of an embodiment(s) herein.

FIGS. 9, 10, 11, 12, 13, 14, 15, 16, 17 and 18 collectively schematically illustrate an example of the member 522, which includes an inner plate 902, an outer plate 904, and the membrane 526, where the membrane 526 is disposed (sandwiched) between the inner plate 902 and the outer plate 904. FIG. 9 schematically illustrates a perspective view of the member 522, and FIG. 10 schematically illustrates an exploded view of the member 522 of FIG. 9.

With reference to FIGS. 9 and 10, the inner plate 902 and the outer plate 904 are aligned with respect to each other such that the second set of openings 524 of the inner plate 902 align with a third set of openings 906 in the outer plate 904. The membrane 526 is adjacent to both the second set of openings 524 of the inner plate 902 and the third set of openings 906 in the outer plate 904 and in fluid communication with the environment outside of the cover connector 106 and inside of the cavity 302. An example of a suitable material includes a material that is liquid-proof and air permeable such as expanded polytetrafluoroethylene (ePTFE) or Teflon®, a product of Chemours, a company headquartered in DE, US, or the like.

The inner plate 902 and the outer plate 904 are affixed to each other via an adhesive such as an epoxy, etc. In general, dimensions (length and width) of the membrane 526 are smaller than dimensions of the inner plate 902 and the outer plate 904 such that the inner plate 902 and the outer plate 904 face each other with no membrane 526 therebetween near perimeters of the inner plate 902 and the outer plate 904. The inner plate 902 and the outer plate 904 are both curved shaped, with the radius of curvature of the inner plate 902 smaller than a radius of curvature of the outer plate 904 such the inner plate 902 fits within the outer plate 904.

In one instance, the membrane 526 includes a thickness in a range of one thousandth of an inch (0.001 inch/0.0254 millimeters, mm) to fifty thousandth of an inch (0.050 inch/1.27 mm) such as six thousandth of an inch (0.006 inch/0.1524 mm), seven thousandth of an inch (0.007 inch/0.1788 mm), eight thousandth of an inch (0.008 inch/0.2032 mm), greater or smaller. The thickness of the epoxy, etc. is such that the membrane 526 is in physical contact with the inner plate 902 and the outer plate 904, but not squeezed such that the thickness of the membrane 526 is reduced outside of predetermined tolerance.

In this example, the second set of openings 524 of the inner plate 902 and the third set of openings 906 in the outer plate 904 have a same pattern. In general, the second set of openings 524 of the inner plate 902 and the third set of openings 906 each include N openings, where N is a positive integer equal to or greater than one. In the illustrated example, N=9, and the second set of openings 524 of the inner plate 902 and the third set of openings 906 of the outer plate 904 each are distributed in a pattern of three adjacent rows, including two outer rows each including two (2) openings and an inner row including five (5) openings. Other patterns are contemplated herein.

In another instance, one or more of the openings can be otherwise located. For instance, the example shows all of the openings about the junction where the "J" shaped profiles of the third side $\mathbf{510}_1$ and the fourth side $\mathbf{510}_2$ abut. In another instance, one or more of the openings can be located at a side $\mathbf{508}_1$ and/or $\mathbf{508}_2$, at the trucks of the "J" shaped profiles of the third side $\mathbf{510}_1$ and the fourth side $\mathbf{510}_2$, etc. In another instance, one or more of the openings can be otherwise shaped. For instance, the example shows all of the openings as circles. In another instance, one or more of the openings can be square, rectangular, elliptical, irregular, and/or otherwise shaped.

In one instance, a size and/or a number of the openings is based on a predetermined range. For example, in one instance the size and/or the number of the openings is such that a total surface area satisfies a predetermined surface area. An example range includes 0.04632 inches squared ($in^2$) (29.88 $mm^2$) to 0.4632 $in^2$ (298.84 $mm^2$), such as 0.1158 $in^2$ (74.71 $mm^2$), etc. Additionally, or alternatively, the size of the openings are configured to mitigate inadvertent damage such as a puncture, a stretching, etc. of the membrane 526 through any of the openings, e.g., by an instrument that may come into contact with the electromechanical connector cover 106. Additionally, or alternatively, the size of the openings are configured to mitigate inadvertent damage such as a puncture, a stretching, etc. of the membrane 526 through any of the openings, e.g., by an instrument that may come into contact with the electromechanical connector cover 106.

Figure 14:
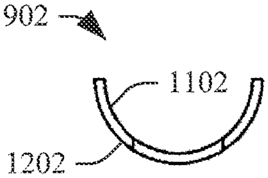
FIG. 14 schematically illustrates an end view of the top portion of the connector cover member, in accordance with an aspect of an embodiment(s) herein.
Figure 15:
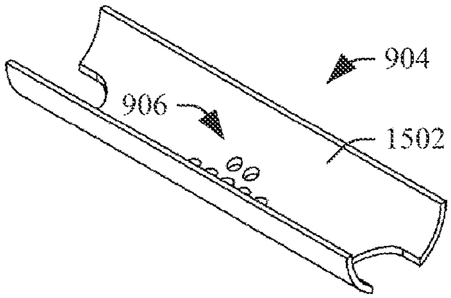
FIG. 15 schematically illustrates a top perspective view of a bottom portion of the connector cover member, in accordance with an aspect of an embodiment(s) herein.
Figure 16:
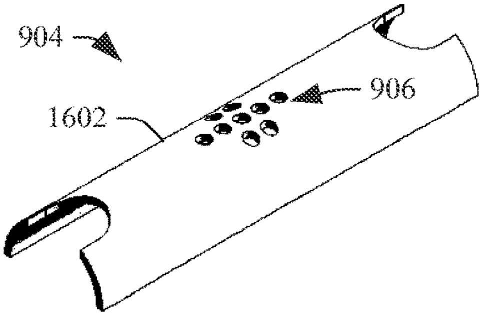
FIG. 16 schematically illustrates a bottom perspective view of the bottom portion of the connector cover member, in accordance with an aspect of an embodiment(s) herein.
Figure 17:
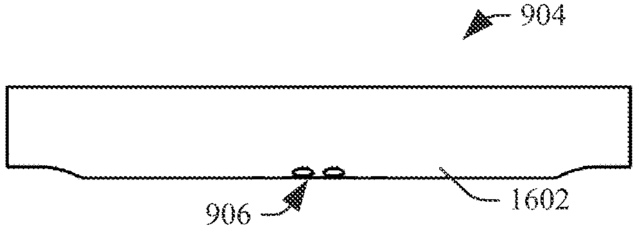
FIG. 17 schematically illustrates a side view from the bottom portion of the connector cover member, in accordance with an aspect of an embodiment(s) herein.

FIGS. 11, 12, 13 and 14 schematically illustrate views of the inner plate 902, respectively including a perspective view of an arc shaped top side 1102 of the inner plate 902 along with the second set of openings 524 (FIG. 11), a perspective view of an arc shaped bottom side 1202 of the inner plate 902 along with the second set of openings 524 (FIG. 12), a side view of the bottom side 1202 of the inner plate 902 along with the second set of openings 524 (FIG. 13), and an end view of the inner plate 902 (FIG. 14).

Figure 18:
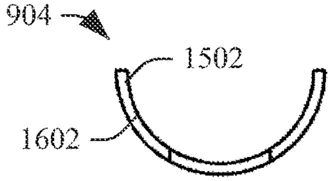
FIG. 18 schematically illustrates an end view of the bottom portion of the connector cover member, in accordance with an aspect of an embodiment(s) herein.

FIGS. 15, 16, 17 and 18 schematically illustrate views of the outer plate 904, respectively including a perspective view of an arc shaped top side 1502 of the inner outer plate 904 along with the third set of openings 906 (FIG. 15), a perspective view of an arc shaped bottom side 1602 of the outer plate 904 along with the third set of openings 906 (FIG. 16), a side view of the bottom side 1602 of the outer plate 904 along with the third set of openings 906 (FIG. 17), and an end view of the outer plate 904 (FIG. 18).

Figure 19:
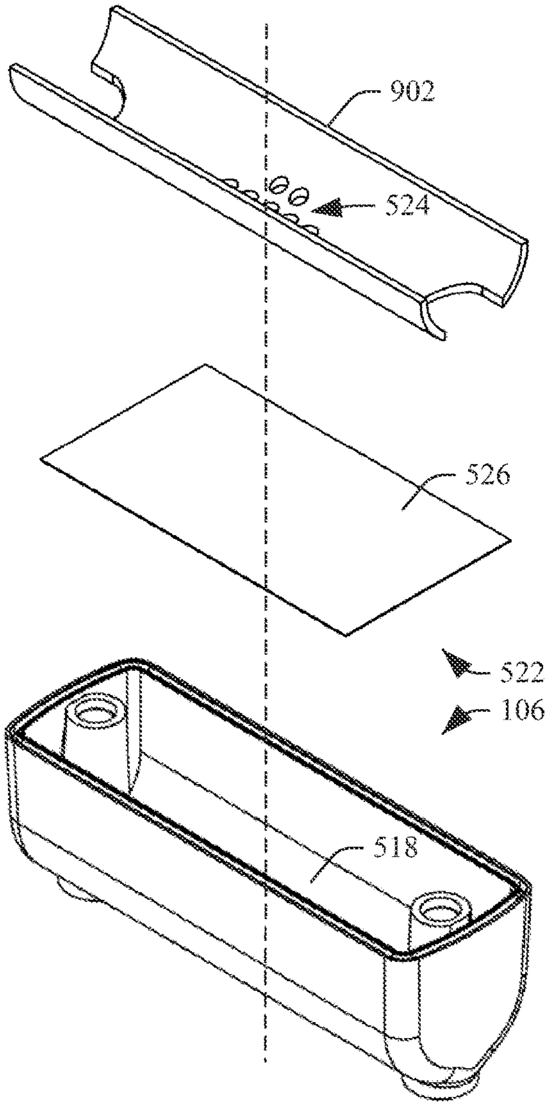
FIG. 19 schematically illustrates a perspective view of another non-limiting example of the connector cover member, in accordance with an aspect of an embodiment(s) herein.

FIG. 19 schematically illustrates a perspective view of another non-limiting example of the connector cover member 522. In FIGS. 9 and 10, the connector cover member 522 includes the inner plate 902 with the second set of openings 524 of the inner plate 902, the outer plate 904 with the third set of openings 906, and the membrane 522 sandwiched therebetween, and the connector cover member 522 attached to the inner region 518. In this example, the outer plate 904 is omitted, and the inner plate 902 is affixed to the inner region 518. Similarly, in one instance, the inner plate 902 is affixed to the inner region 518 via an adhesive such as an epoxy, etc. For example, in one instance dimensions (length and width) of the membrane 526 are smaller than dimensions of the inner plate 902, and a region near the perimeter of the inner plate 902 is affixed to the inner region 518 via an adhesive. Optionally, areas of the membrane 526 outside of areas near the second set of openings 524 of the inner plate 902 are affixed to the inner region 518 and/or the inner plate 902 via an adhesive such as an epoxy.

Figure 20:
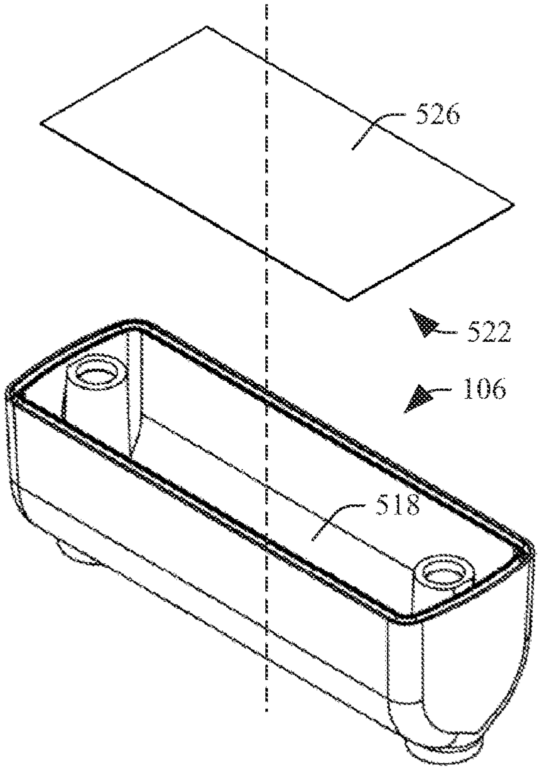
FIG. 20 schematically illustrates a perspective view of yet another non-limiting example of the connector cover member, in accordance with an aspect of an embodiment(s) herein.

FIG. 20 schematically illustrates a perspective view of another non-limiting example of the connector cover member 522. In FIGS. 9 and 10, the connector cover member 522 includes the inner plate 902 with the second set of openings 524 of the inner plate 902, the outer plate 904 with the third set of openings 906, and the membrane 522 sandwiched therebetween, and the connector cover member 522 attached to the inner region 518. In this example, the inner plate 902 and the outer plate 904 are omitted, and the membrane 526 is affixed to the inner region 518. Similarly, in one instance the membrane 526 is affixed to the inner region 518 via an adhesive such as an epoxy, etc.

Figure 21:
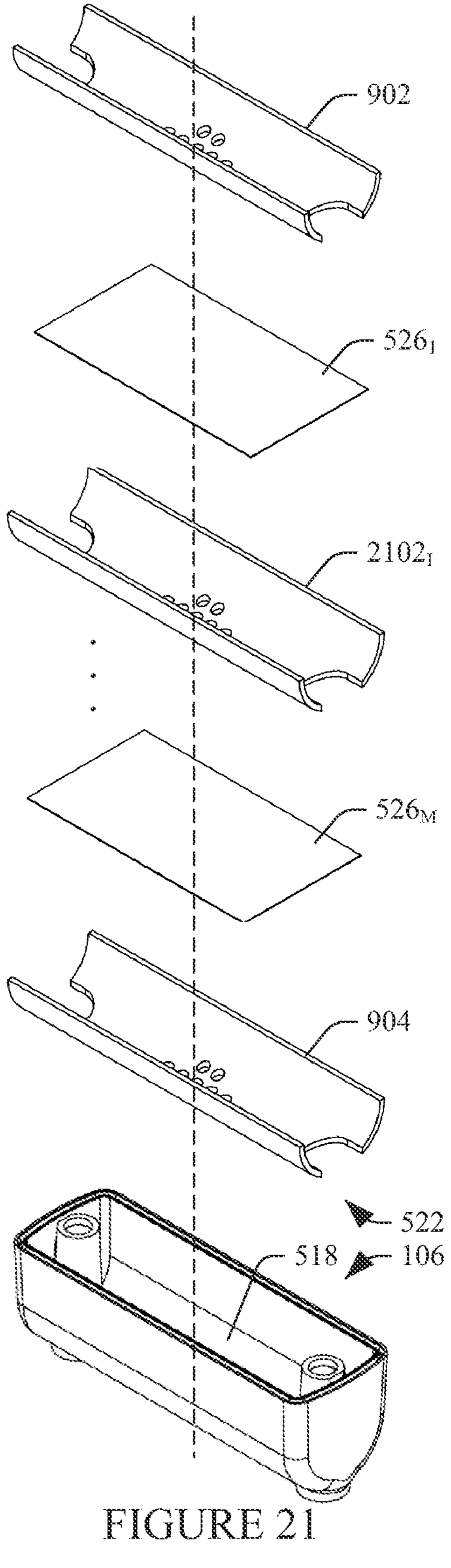
FIG. 21 schematically illustrates a perspective view of still another non-limiting example of the connector cover member, in accordance with an aspect of an embodiment(s) herein.

FIG. 21 schematically illustrates a perspective view of another non-limiting example of the connector cover member 522. In FIGS. 9 and 10, the connector cover member 522 includes the inner plate 902 with the second set of openings 524 of the inner plate 902, the outer plate 904 with the third set of openings 906, and the membrane 522 sandwiched therebetween, and the connector cover member 522 attached to the inner region 518. In this example, the connector cover member 522 includes a plurality of M membranes 526, including a membrane $\mathbf{526}_1, \ldots, \mathbf{526}_M$, the inner plate 902, the outer plate 904, and L intermediate plates, including an intermediate plate . . . , $\mathbf{2102}_I$, . . . , where M and L and I are positive integers, and M is greater than L, and M equals L plus two such that there is one more plate than membrane. Similarly, the members are affixed to each other and the member 522 is affixed to the inner region 518 via an adhesive such as an epoxy.

Figure 22:
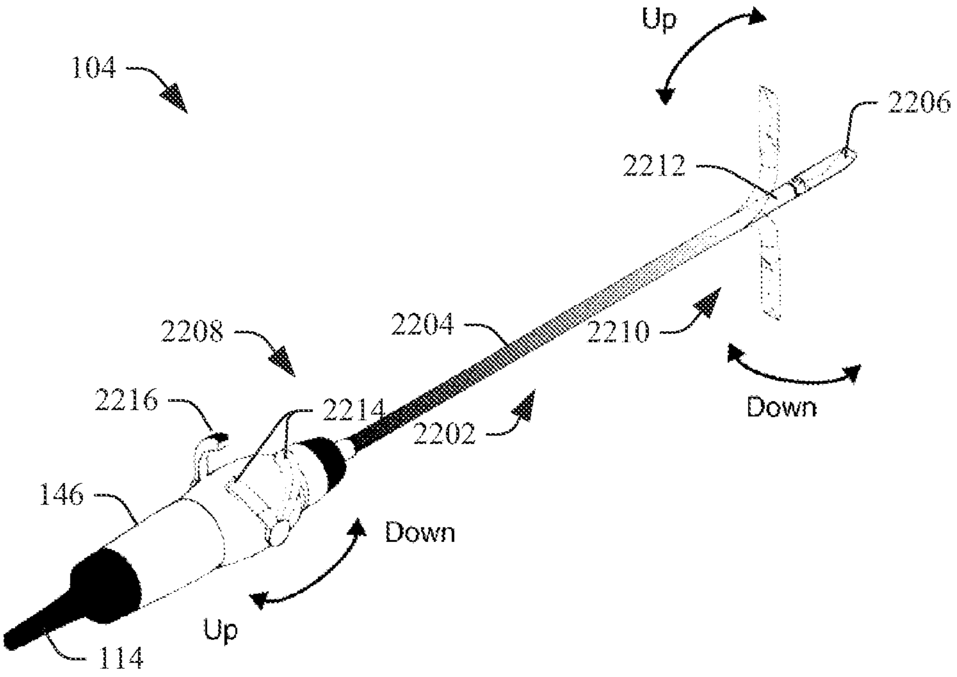
FIG. 22 schematically illustrates a non-limiting example of a laparoscopic ultrasound probe with articulating member showing up and down movement of the articulating member, in accordance with an aspect of an embodiment(s) herein.
Figure 23:
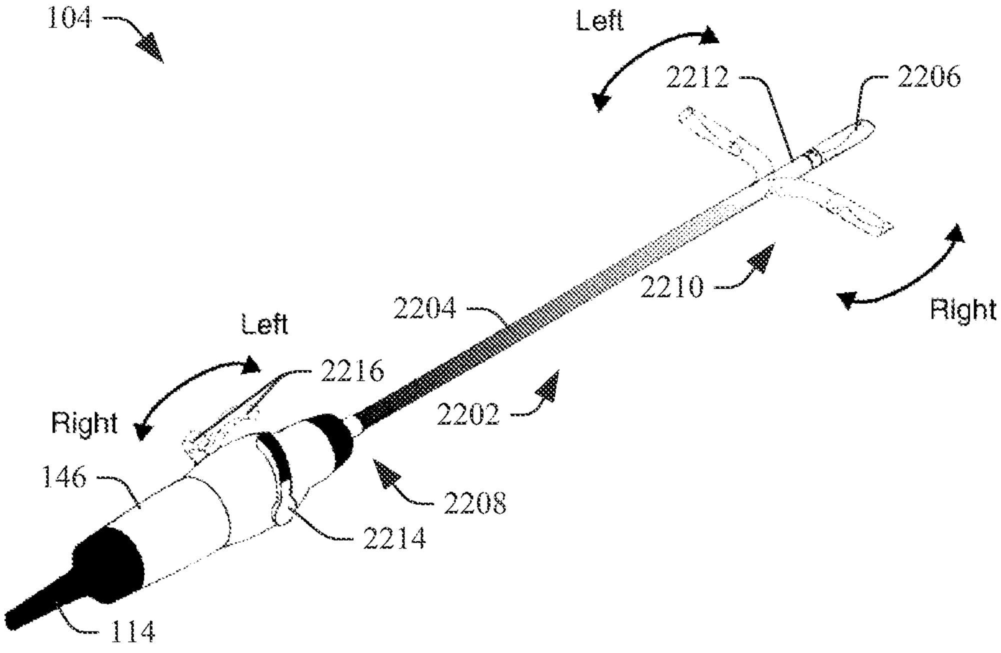
FIG. 23 schematically illustrates a non-limiting example of the laparoscopic ultrasound probe of FIG. 22 showing left and right movement of the articulating member, in accordance with an aspect of an embodiment(s) herein.
Figure 24:
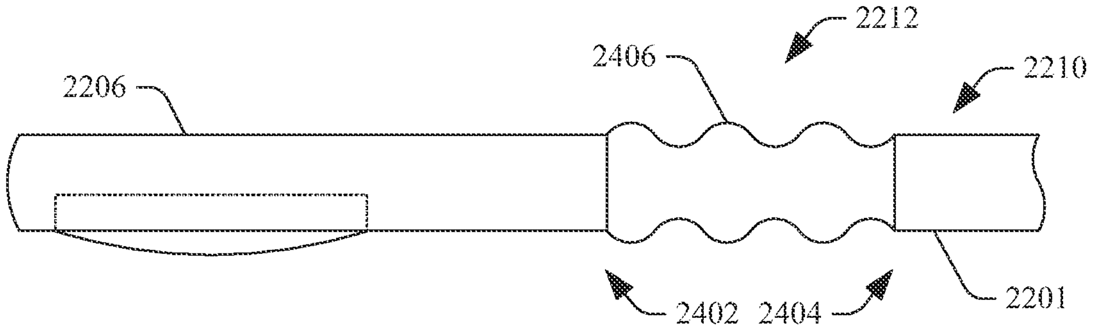
FIG. 24 schematically illustrates a non-limiting example of the laparoscopic ultrasound probe of FIGS. 22 and 23 with a boot seal over the articulating member, in accordance with an aspect of an embodiment(s) herein.

FIGS. 22, 23 and 24 schematically illustrate an example of the ultrasound imaging probe 102 configurated as an articulating laparoscopic probe. FIG. 22 illustrates a perspective view of the ultrasound imaging probe 102 showing up and down articulation. FIG. 23 illustrates a perspective view of the ultrasound imaging probe 102 showing right and left articulation. FIG. 24 schematically illustrates a magnified view of a portion of the ultrasound imaging probe 102 with the articulating member.

The ultrasound imaging probe 102 includes the handle 146 and an elongated shaft 2202. The elongated shaft 2202 includes a body 2204 and a probe head 2206, both aligned along a long axis of the ultrasound imaging probe 102. The body 2204 includes a first end 2208 and a second opposing end 2210. The first end 2208 of the body 2204 is affixed to the handle 146. An articulating member 2212 couples the second opposing end 2210 of the body 2204 and the probe head 2206.

In the illustrated embodiment, the articulating member 2212 articulates in at least four directions (up, down, right and left). In a variation, the articulating member 2212 articulates in at least two directions. In a variation, the articulating member 2212 is omitted from the probe head 2206, which does not articulate. The handle 146 includes a first actuator 2214 and a second actuator 2216. The first actuator 2214 actuates the articulating member 2212 to control up/down movement of the probe head 2206. The second actuator 2216 actuates the articulating member 2212 to control left/right movement of the probe head 2206.

Examples of such a probe is the I12C4f (9066) 4-Way Laparoscopic Transducer, the I13C3f (9076) Advanced Laparoscopic Transducer, the I13C3fx (9078) Advanced Laparoscopic Transducer with Tracking, and the X18L5s (9009) Hockey Stick Transducer, all products of B-K Medical ApS, a company of Herlev, Denmark, which is a wholly owned subsidiary of General Electric Healthcare, a company of WI, USA. Other laparoscopic probes are also contemplated herein.

FIG. 24 schematically illustrates a magnified view of a portion of the ultrasound imaging probe 102 with the articulating member 2212. The illustrated portion includes the articulating member 2212, the probe head 2206 disposed at a first end region 2402 of the articulating member 2212, and the second end 2210 of the body 2204 disposed at a second end region 2404 of the articulating member 2212. The articulating member 2212 includes a seal 2406, which encloses the articulating member 2212, such as a rubber boot seal or the like.

Examples of approaches for articulating a head of a transducer probe are described in U.S. Pat. No. 9,897,694 B2, filed Jul. 12, 2011, and entitled “Ultrasound Imaging Probe,” and U.S. Pat. No. 10,383,598 B2, filed Jan. 14, 2013, and entitled “Ultrasound Imaging Probe,” both of which are incorporated herein by reference in their entireties.

FIG. 25 illustrates a non-limiting example of a flow chart for a computer-implemented method based at least on speckle statistics. It is to be appreciated that the ordering of the acts in the method is not limiting. As such, other orderings are contemplated herein. In addition, one or more acts may be omitted, and/or one or more additional acts may be included. At 2502, the electromechanical connector cover 106 is installed over the electromechanical connector 116 of an ultrasound imaging probe 102, as disclosed herein and/or otherwise. At 2504, the ultrasound imaging probe 102, including the electromechanical connector 116 with the electromechanical connector cover 106 is cleaned and disinfected, as disclosed herein and/or otherwise. For example, in one instance this includes submerging the ultrasound imaging probe 102, including the electromechanical connector 116 with the electromechanical connector cover 106, in a chemical based cleaning and disinfection fluid, such as a fluid including hydrogen peroxide, etc. At 2506, the ultrasound imaging probe 102, including the electromechanical connector 116 with the electromechanical connector cover 106 is sterilized, as disclosed herein and/or otherwise. For example, in one instance this includes exposing the ultrasound imaging probe 102, including the electromechanical connector 116 with the electromechanical connector cover 106, to a pressure difference, such as a vacuum.

Another example method includes installing an electromechanical connector cover over an electromechanical connector of an ultrasound imaging probe, wherein the electromechanical connector cover is air-permeable and liquid proof, submerging the ultrasound imaging probe with the installed electromechanical connector cover in a liquid during a first part of a reprocessing process, and subjecting the ultrasound imaging probe to air pressure during a second part of the reprocessing process. In one instance, the first part includes a cleaning and disinfection process. In another instance, the liquid includes hydrogen peroxide. In another instance, the second part includes a sterilization process. In another instance, the air pressure includes a vacuum.

As discussed herein, with an invasive procedures such as laparoscopic procedures the laparoscopic ultrasound imaging probe contacts bodily fluids. As such, after an invasive procedure, the ultrasound imaging probe is reprocessed through cleaning, disinfection and sterilization, which includes submerging the ultrasound imaging probe, including the electromechanical connector, in an environment that includes chemicals such as hydrogen peroxide and in an environment that includes pressure differences such as a vacuum. Also discussed herein, a connector cover is installed over the electromechanical connector ultrasound imaging probe to inhibit an ingress of liquids such as the chemicals utilized for the cleaning and disinfection portion of the reprocessing, and then removed for sterilization to allow egress of gasses such as air out of the electromechanical connector under the vacuum of the sterilization portion of the reprocessing. As discussed herein, if the connector cover is not removed before sterilization, a pressure difference generated during sterilization between the inside of the ultrasound imaging probe and the surrounding environment may result in bursting of the rubber boot seal of the articulating member.

An exiting approach to prevent such an event from occurring includes specifying in the maintenance manual instructions that indicate that the connector cover should be installed on the electromechanical connector during cleaning and disinfection and that the connector cover should not be installed on the electromechanical connector during sterilization, which is subject to human error, which may result in ultrasound imaging probe downtime and/or increased cost associated with repairing and/or replacing the compromised ultrasound imaging probe. With approach described herein, the connector cover 106 includes a member 522 housing a liquid-proof and an air-permeable membrane 526, which inhibits ingress of fluid during the cleaning and disinfection process and allows egress of gas during the sterilization process. As such, the connector cover 106 can remain on during the entire reprocessing process, mitigating damage to the ultrasound imaging probe 102, such as damaging the rubber boot seal 2406 of the articulating member 2210 during sterilization when the connector cover 106 is on, which can reduce downtime of a compromised ultrasound imaging probe 102 and/or can reduce overall correction maintenance cost associated with repairing and/or replacing a compromised ultrasound imaging probe 102.

The above can be implemented by way of computer readable instructions, encoded, or embedded on the computer readable storage medium, which, when executed by a computer processor, cause the processor to carry out the described acts or functions. Additionally, or alternatively, at least one of the computer readable instructions is carried out by a signal, carrier wave or other transitory medium, which is not computer readable storage medium.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include such additional elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only and are thus not intended to limit in any way the definition and/or meaning of the term "computer." The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present disclosure. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used in practice as some jurisdictions require them, but this should not be taken to mean that the features in the dependent claims are mutually exclusive.

What is claimed is:

1. An electromechanical connector cover for covering an electromechanical connector of an ultrasound imaging probe, comprising:

a three-dimensional container, including:

a cavity configured to receive the electromechanical connector, the cavity including:

a rim configured to provide a hermetic seal with the received electromechanical connector;

at least one side with at least one opening;

a membrane disposed in the cavity and adjacent to the at least one opening, wherein the membrane is liquid-proof and air-permeable; and a first plate, wherein the membrane is disposed between the first plate and the at least one side; and a member housing the membrane, wherein the member includes the first plate.

2. The electromechanical connector cover of claim 1, the first plate including: at least one opening, wherein the at least one opening of the first plate and the at least one opening of at least one side are spatially aligned.

3. The electromechanical connector cover of claim 2, the member further including:

a second plate, wherein the membrane is disposed between the first plate and the second plate, and the second plate is disposed at the at least one side.

4. The electromechanical connector cover of claim 3, the second plate including: at least one opening, wherein the at least one opening of the second plate and the at least one opening of the at least one are spatially aligned.

5. The electromechanical connector cover of claim 3, further including:

an adhesive between the first plate and the second plate.

6. The electromechanical connector cover of claim 1, further including:

an adhesive between the member and the at least one side.

7. The electromechanical connector cover of claim 1, the at least one side including:

an outer convex face; and an inner convex surface inside of the cavity, wherein the at least one opening extends entirely through the at least one side.

8. The electromechanical connector cover of claim 1, wherein the membrane includes expanded polytetrafluoroethylene.

9. The electromechanical connector cover of claim 1, further includes:

a mechanical fastener configured to engage a complementary locking mechanism of the electromechanical connector to fasten the electromechanical connector cover and the electromechanical connector together.

10. The electromechanical connector cover of claim 1, further includes:

a mechanical seal disposed on the rim of the cavity and sandwiched the electromechanical connector cover and the received electromechanical connector.

* * * * *